United States Patent
Burk et al.

(10) Patent No.: US 6,508,753 B2
(45) Date of Patent: Jan. 21, 2003

(54) CHIRAL LIGANDS FOR ASYMMETRIC CATALYSIS

(75) Inventors: Mark Joseph Burk, San Diego, CA (US); Christophe Guillaume Malan, Le Pradet (FR)

(73) Assignee: Chirotech Technology Limited, Cambridge (GB)

( * ) Notice: Subject to any disclaimer, the term of this patent is extended or adjusted under 35 U.S.C. 154(b) by 45 days.

(21) Appl. No.: 09/873,652

(22) Filed: Jun. 4, 2001

(65) Prior Publication Data

US 2002/0035285 A1 Mar. 21, 2002

(30) Foreign Application Priority Data

Jun. 2, 2000  (GB) .............................. 0013546
Jul. 24, 2000 (GB) .............................. 0018145
Jan. 19, 2001 (GB) .............................. 0101458

(51) Int. Cl.$^7$ .............................. C07F 9/02; B01J 31/00

(52) U.S. Cl. .......................... 566/18; 556/23; 564/398; 568/17; 568/799; 568/814; 585/275; 585/277

(58) Field of Search ...................... 556/18, 23; 568/17, 568/799, 814; 585/275, 277; 564/398; 502/155, 162

(56) References Cited

U.S. PATENT DOCUMENTS

| 3,798,241 A | 3/1974 | Kagan et al. ............. 260/340.9 |
| 5,530,150 A | 6/1996 | Takaya et al. ................. 556/18 |
| 5,801,261 A | 9/1998 | Laue et al. ................... 556/16 |
| 5,847,222 A | 12/1998 | Yokozawa et al. ............ 556/16 |

OTHER PUBLICATIONS

Schmid, Rudolf, Emil A. Broger, Marco Cereghetti et al., (1996) "New developments in enantioselective hydrogenation" *Pure and Applied* Chemistry 68(1):131–138.

Schmid, Rudolf, Marco Cereghetti, Bernd Heiser et al. (1988) "Axially Dissymmetric Bis(triaryl)phosphines in the Biphenyl Series:: Synthesis of (6'6'–Dimethylbiphenyl–2, 2'–diyl)bis(diphenylphosphine) ('BIPHEMP') and Analogues, and their Use in RH(1)–Catalyzed Asymmetric Isomerizations of N,N–Diethylnerylamine" *Helvetica Chimica Acta* 71:897–929.

Hwang, Der–Ren, Cheu–Pyend Chen and Biing–Jiun Uang (1999) Aerobic catalytic oxidative coupling of 2–naphthols and phenols by VO(acac)$_2$ *Chem. Commun.*, pp. 1207–1208.

*Primary Examiner*—Porfirio Nazario-Gonzalez

(57) ABSTRACT

A novel phosphine ligand is an enantiomerically enriched compound of formula 5

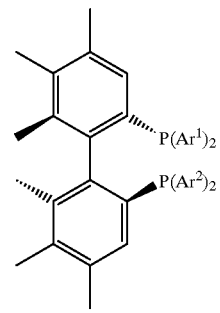

or the opposite enantiomer thereof, wherein $Ar^1$ and $Ar^2$ represent the same or different aromatic groups of up to 20 C atoms. A transition metal complex of this ligand is useful as a catalyst in stereoselective hydrogenation.

16 Claims, No Drawings

CHIRAL LIGANDS FOR ASYMMETRIC CATALYSIS

FIELD OF THE INVENTION

This invention relates to improved phosphine ligands and catalysts derived therefrom that are useful for asymmetric hydrogenation processes.

BACKGROUND OF THE INVENTION

Asymmetric hydrogenation is an important reaction for providing chiral intermediates for pharmaceutical agents, and other products useful in the life sciences, required in the necessary single stereoisomer form. In particular the reaction provides economically viable manufacturing processes because the raw materials can be inexpensive, the reaction conditions are simple, and the catalyst may be used at a very low loading.

The diversity of substrates amenable to transformation into enantiomerically enriched chiral products by asymmetric hydrogenation means that a complementary range of catalysts is required in order to find the best match of substrate and catalyst for a given application. One class of catalysts that has received considerable attention is transition metal complexes of so-called biaryl diphosphine ligands represented by general formulae 1 and 2 Such ligands typically, although not always, possess a plane of symmetry and exist as stable atropisomers by virtue of hindered rotation about the C—C bond between the two aromatic rings bearing the phosphine groups. As a consequence these ligands have great utility for asymmetric catalysis when used in enantiomerically pure form. In particular, ruthenium complexes of the ligands are well suited to the asymmetric hydrogenation of C=X bonds, wherein X is a heteroatom, typically oxygen or nitrogen. Substrates possessing such functionality include, but are not limited to, β-keto esters, β-diketones, aromatic ketones, imines and oximes.

In the subclass of biaryl phosphines represented by formula 2, the presence of small substituents at 6- and 6'-positons, e.g. $R^1$ is methyl or methoxy, is sufficient to confer atropisomerism. Prototype ligands of this subclass are BIPHEMP (3) (U.S. Pat. No. 3,798,241 and Schmid et al, Helv. Chim. Acta, 1988, 71, 897) ad BIPHEP (4) (Schmid et al., Pure & Appl. Chem., 1996, 68, 131). Numerous variants have been reported in which extra substitution occurs on the phenyl rings bearing the phosphine groups (i e at least one of $R^2$–$R^4$ is not hydrogen) and/or the diphenylphosphino groups are replaced with other diarylphosphino groups. Variants of this nature can profoundly effect the electronic and stearic properties of the ligand, which may in turn alter the efficiency and selectivity of derived catalysts Representative examples are described in U.S. Pat. Nos. 5,847,222 and 5,801,261

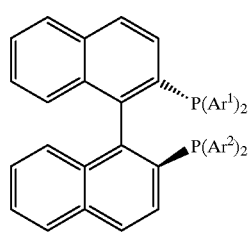

(1)

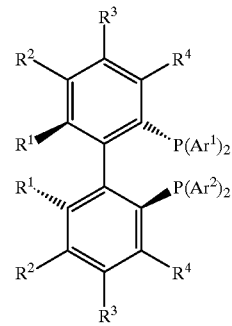

(2)

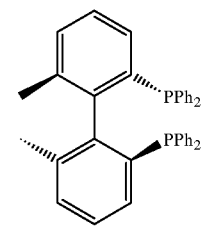

(3)

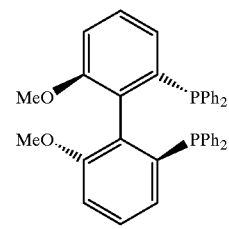

(4)

For application in industrial asymmetric catalysis, an asymmetric hydrogenation catalyst comprising a transition metal complex of a chiral ligand needs to exhibit high activity and enantioselectivity in the desired transformation of a particular substrate. It is equally important that the chiral ligand precursor can be prepared efficiently by a synthetic route that is amendable to scale-up. Although a very large number of chiral phosphine ligands have been prepared and investigated in small quantities for research, a much lesser number have been developed commercially and in such context synthetic accessibility can often be the limiting factor Of the biaryl diphosphines reported in the literature, only the BINAP (1) and BIPHEP (4) systems have been developed sufficiently for large-scale industrial use. In contrast, the reported synthetic route to BIPHEMP (3) (Schmid et al., 1988) appears unsuitable for scale-up. A particular problem with this route is the tendency for optically pure intermediates to racemise during the latter stages of the route.

SUMMARY OF THE INVENTION

The present invention is based on the unexpected discovery that novel [4,4',5,5',6,6'-hexamethyl(1,1'-diphenyl)-2,2'-diyl]bis(diarylphosphine)ligands of formula 5, and the opposite enantiomers thereof, have utility as components of catalysts for asymmetric synthesis (5)

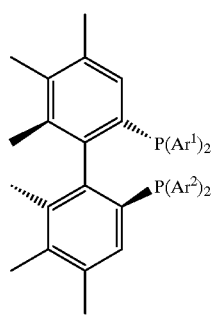

In particular, transition metal complexes of the ligand (5) can give superior performance in the asymmetric hydrogenation of certain prochiral substrates, in terms of improved enantioselectivity and/or catalytic activity, when compared with equivalent complexes of alternative biaryl diphosphine ligands. The ligand (5) is prepared efficiently via phenolic coupling.

DESCRIPTION OF THE INVENTION $Ar^1$ and $Ar^2$ in formula (5) represent aromatic groups of up to 20 C atoms, which may be either the same or different groups. Preferred compounds of the present invention are those where $Ar^1$ and $Ar^2$ are the same and both are phenyl, optionally substituted with one, two or more alkyl or alkoxy groups (e.g. para-tolyl,3,5-dimethylphenyl, 4-methoxy-3,5-dimethylphenyl) and ruthenium complexes thereof. Typically, the complexes will be of the form $Ru(5)X_2$, wherein X is selected from halide (e.g. chloride), carboxylate (e.g. trifluoroacetate) or an allylic radical (e.g. methallyl) Such ruthenium complexes can also incorporate chiral diamine ligands and have particular utility in the asymmetric hydrogenation, in the presence of base, of certain ketones and imines Cationic rhodium complexes of (5), e.g $[Rh(5)COD]BF_4$, can also be prepared.

Without wishing to be bound by theory, the unique properties of the ligand 5 might be attributable to the buttressing effects of three methyl groups at adjacent positions of each phenyl ring in the biaryl moiety. The proximity of these groups means that at least one of the groups may be forced out of plane with the phenyl ring, in order to relieve non-bonded interactions. In turn, this stearic crowding may serve to influence the P-Ru-P bite angle in complexes thereof. The same methyl groups may also exert an electronic effect, by making the phenyl rings in the biaryl moiety and in turn the complexed ruthenium atom more electron-rich. Such an effect may be manifested through enhanced enantioselectivity in the hydrogenation of electron-deficient substrates such as the olefin (α) or β-ketoester (b).

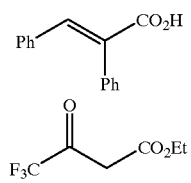

More generally, a substrate to be hydrogenated may have at least one C=O, C=N or C=C bond. For example, the substrate is a ketone and the product is a chiral alcohol. The substrate may be prochiral, and the product generated in enantiomerically enriched form, e.g. in an enantiomeric excess (ee) of at least 70%, 80% or 90%.

Another advantage of the present invention is that the ligands of type 5 may be assembled rapidly by a concise synthetic route, as represented in Scheme 1. The route commences with the oxidative phenolic coupling of commercially available 3,4,5-trimethylphenol (7). The symmetry and substitution pattern of this phenol ensures that only a single regioisomer is formed in this reaction, which may be effected conventionally with stoichiometric reagents such as $FeCl_3$, according to the method of Takaya et al. (U.S. Pat. No. 5,530,150), although catalytic reagents such as V(O)acac$_2$ (Hwang et al., *Chem. Commun.,* 1999, 1207) provide a viable alternative. The resulting diol (8) is converted to an activated derivative suitable for use in a coupling reaction to form carbon-phosphorus bonds. For convenience, the activated derivative may be the bis-triflate (9). Completion of the synthesis then entails coupling with either a diarylphosphine, a diarylphosphine oxide or synthetic equivalents thereof. For expediency the coupling is carried out with a diaryiphosphine under conditions in which both carbon-phosphorus bonds are formed. Alternatively, formation of each carbon-phosphorus bond in a separate step, via 10 or 11, allows the introduction of different diarylphosphino groups. The use of diarylphosphine oxide reagents necessitates one or two extra steps (reduction) to provide the ligand (5), although the adducts (11), (12) and (13) are amenable to resolution into constituent enantiomers by formation of an inclusion complex with a chiral resolving agent. It will be recognized by a skilled practitioner that other methods are applicable in order to obtain the ligand (5) in enantiomerically enriched form. For example, preparative chiral chromatography may be used to directly resolve (5) or any of the intermediates shown in Scheme 1; in the case of diol (8), resolution by biocatalysis is also applicable. The skilled practitioner will also recognise that alternative routes to the ligand (5) are applicable, for example, via Ullmann coupling of the bis-phosphine oxide (14) wherein X is a bromo or iodo group.

Scheme 1

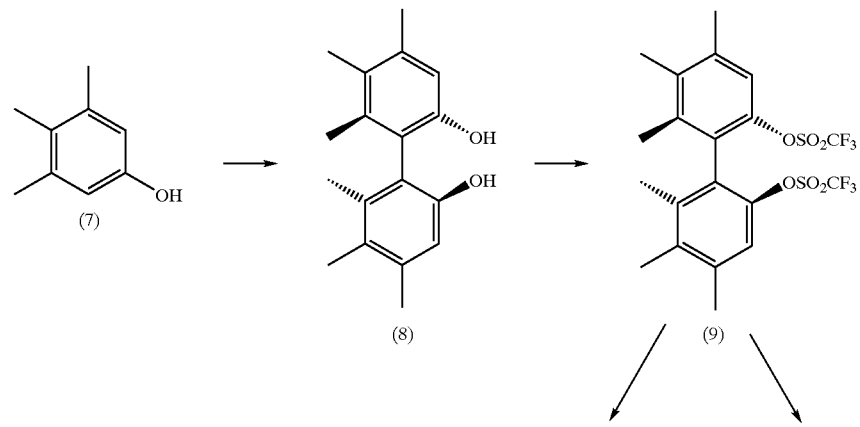

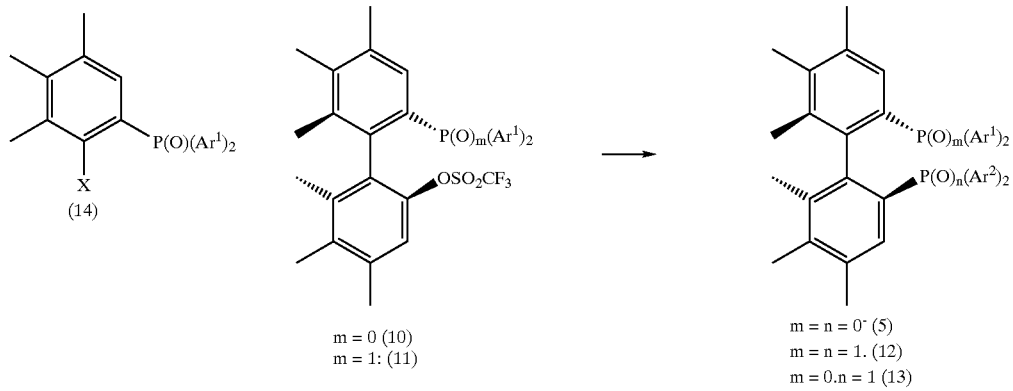

m = 0 (10)
m = 1: (11)

m = n = 0 (5)
m = n = 1. (12)
m = 0.n = 1 (13)

The invention is illustrated by the following Examples.

EXAMPLE 1

3,3',4,4',5,5'-Hexamethyl-1,1'-bi-2-phenol

A 100 mL Schlenk flask equipped with a stirring bar is loaded with 3,4,5-trimethylphenol (Lancaster, 2.0 g, 14.7 mmol) and dichloromethane (40 mL) is added followed by V(O)acac$_2$ (Aldrich, 800 mg, 30 mmol). On the top of the flask is placed an adapter fitted with a tap and connected to a double balloon of oxygen gas. The flask is evacuated under reduced pressure and purged with oxygen. This operation is repeated two times and the dark green reaction mixture stirred rapidly for 18 h. At this point, an aliquot shows>95% conversion of the starting material. The mixture is filtered over Celite™, the filter cake washed well with dichloromethane (ca, 100 mL). The filtrate is evaporated to dryness under reduced pressure, taken-up in acetone (25 mL) and filtered again on Celite™ The filtrate is evaporated to dryness under reduced pressure and the residue triturated with methanol (10 mL). The precipitate is collected and washed with MeOH (2.1 mL). The filtrate is evaporated to dryness under reduced pressure and the residue treated as above (3 times with 5, 4 and 4 mL of methanol) The collected residue (167 g, 84% yield) is the desired biphenol as grey crystals, mp: 235–237° C. (cf U.S. Pat. No. 5,530, 150 231–233° C.); $^1$H—NMR (CDCl$_3$, 400 MHz): 1.90 (s, 3H); 2.15 (s, 3H); 2.30 (s, 3H); 4.50 (s, 1H), 6.75 (s, 1H), $^{13}$C—NMR(CDCl$_3$, 100 MHz). 15.4; 16.9; 20.9, 114.3, 118.0; 127.7; 136.8; 138.4, 151.2

EXAMPLE 2

3,3',4,4',5,5'-Hexamethyl-1,1'-bi-2-phenol-bis-trifluoromethylsulfonate

A dry 5 mL one neck flask equipped with a stirring bar under nitrogen is loaded with the biphenol (190 mg, 0.70 mmol), 4-N,N-dimethylaminopyridine (Aldrich, 26 mg, 0.21 mmol) and dry dichloromethane (Aldrich, 2 mL). The flask was immersed in an ice-water bath and 2,6-dimethylpyridine (0.180 mL, 1.55 mmol) was added with stirring, followed by trifluoromethanesulfonic anhydride (0.260 mL, 1.55 mmol). The starting suspension soon developed to a slightly brown solution and stirring at 0° C. pursued for 2 h. At that time, the solution was evaporated to dryness under reduced pressure, redissolved in dichloromethane and filtered over a silica gel. The filtrate is evaporated to dryness under reduced pressure and delivers the desired ditriflate as pate yellow crystals (354 mg, 95% yield), mp. 92–93° C. (Takaya et al., U.S. Pat. No. 5,530, 150. 90–91° C.), $^1$H—NMR (CDCl$_3$, 400 MHz). .00 (s, 3H), 2.25 (s, 3H), 2.40 (s, 3H), 7.05 (s, 1H); $^{13}$C—NMR (CDCl$_3$, 100 MHz): 15.9, 17.6, 20.9; 118.3 ($^1J_{C-F}$318 Hz), 119.7, 125.9; 136.1, 138.7; 138.9, 145.0.

EXAMPLE 3

3,3',4,4',5,5'-Hexamethyl-6-diphenylphosphinyl-6'-trifluoromethanesulfonyloxybiphenyl To a dry, 100 mL dry Schlenk flask equipped with a stirring bar were sequentially added the ditriflate (1.07 g, 2.0 mmol), diphenylphosphinoxide (1.21 g, 6.0 mmol), palladium acetate (90 mg, 0.4 mmol), 1,4-bis-diphenylphosphinobutane (340 mg, 0.8 mmol) under a flux of N$_2$ A septum was placed on the top of the flask and dimethyl sulfoxide (7 mL) and diisopropylethylamine (2.1 mL, 12 mmol) were quickly added with stirring. The reaction mixture was heated at 110° C. during 16 h (TLC (diethyl ether) shows almost full conversion), cooled to room temperature and evaporated to dryness under reduced pressure and gentle heating. The greenish-yellow residue was subjected to flash chromatography (diethyl ether) to give the title compound (1.030 g, 1.6 mmol) in 80% yield; $^1$H—NMR (CDCl$_3$, 400 MHz) 1.75 (s, 3H); 1.90 (s, 3H), 2.05 (s, 3H), 2.20–2.30 (3.s, 9H), 6.55 (s, 1H), 7.15 (d, 1H); 7.25–7.6 (m, 10H); $^{31}$P—NMR (CDCl$_3$, 162 MHz) 29.1.

A portion (0.86 g) of this material was subjected to preparative chiral HPCL to furnish 0.33 and 0.34 g of each enantiomer with >99% enantiomeric purity. The method is the following: Chiralpak AD; heptane/2-propanol, 95/5; detection at 254 nm; flow 22 mL mm$^{-1}$; temperature ambient.

EXAMPLE 4

(R)-3,3',4,4',5,5'-Hexamethyl-6-diphenylphosphonyl-6'-trifluoromethanesulfonyloxy-biphenyl To a dry 100 mL Schlenck flask equipped with a stirring bar was added the (R)-diphenylphosphinoxide (400 mg, 0.63 mmol), dry and degassed o-oxylene (10 mL) and triethylamine (3.5 mL, 25.2 mmol). The Schlenck flask was placed in an ice bath and allowed to cool there for 15 min. Trichlorosilane (3.4 mL, 25 mmol) was added dropwise over 5 min and a vigorous reaction ensued. The Schlenck flask was then put in an oil bath at 120° C. and stirred vigorously for 20 h. The mixture was allowed to cool to room temperature and aqueous NaOH (2M, 80 mL) was added carefully over 1 h. The mixture obtained was extracted with toluene (2×50 mL), the organic phase washed with aqueous HCl (1M, 2×50 mL), distilled $H_2O$ (2×50 mL) and brine (50 mL) and dried with $MgSO_4$. After evaporation of the volatiles to dryness, a colourless oil was obtained (390 mg, >95% yield) that was used without further purification in the next step. $^1H$—NMR ($CDCl_3$, 400 MHz): 1.85 (s, 3H); 2.0 (s, 3H); 2.15 (2×s, 6H); 2.20 (s, 3H); 2.25 (s, 3H); 6.75 (m, 1H); 6.9 (s, 1H); 7.0–7.20 (m, 10H); $^{31}P$—NMR ($CDCl_3$, 162 MHz): −11.8.

EXAMPLE 5

(R)-3,3',4,4',5,5'-Hexamethyl-6,6'-bis-diphenylphosphonylbiphenyl

Method (a)

To a dry, 25 mL Schlenck flask with a stirring bar under nitrogen atmosphere were sequentially added $NiCl_2dppe$ (32 mg, 0.06 mmol), dry dimethylformamide (1.5 mL) and diphenylphosphine (0.15 mL, 0.87). The flask was placed in an oil bath at 100° C. and the mixture stirred for 30 min. A solution of starting (R)-triflate (380 mg, 0.58 mmol) and DABCO (170 mg, 1.51 mmol) in dry dimethylformamide (2 mL, +0.5 mL rinse) was added and the mixture stirred at 100° C. for 16 h. Volatiles were evaporated off under vacuum and the resulting reddish-brown oil directly submitted to flash chromatography on silica gel with heptane/dichloromethane as eluant This furnished 160 mg of the product as white foam (40%). $^1H$—NMR ($CDCl_3$, 400 MHz): 1.60 (s, 6H); 2.0 (s, 6H); 2.25 (s, 6H); 6.85 (m, 2H); 7.15–7.35 (m, 20H); $^{31}P$—NMR ($CDCl_3$, 162 MHz): −13.3.

Method (b)

To a dry 250 mL Schlenck flask with a stirring bar under nitrogen atmosphere were sequentially added $NiCl_2appe$ (250 mg, 0.47 mmol), dry dimethylformamide (15 mL) and diphenylphosphine (2.1 mL, 12.0 mmol) The flask was placed in an oil bath at 100° C. and the mixture stirred for 30 min A solution of starting optically pure triflate (4.5 g, 7.9 mmol) and DABCO (1.29 g, 11.5 mmol) in dry dimethylformamide (25 mL, +2×5 mL rinse) was added and the mixture stirred at 110° C. for 16 h ($^1H$— and $^{31}P$—NMR shows full starting material conversion). Volatiles were evaporated off under high vacuum at 100–120° C. and the resulting reddish-brown oil was dissolved in dichloromethane (100 mL), washed with water (50 mL). The aqueous phase was back-extracted with dichloromethane (2×25 mL). The mixed organic phases were washed with HCl (2M, 2×40 mL), water (2×40 mL), dried over magnesium sulfate, filtered and evaporated to dryness. The residue was taken up in dichloromethane and filtered through a pad of silica gel. Evaporation of the filtrate gave 3.2 g of the pure title compound Elution of the silica pad with diethyl ether followed by evaporation of the filtrate gave a mixture (2.5 g) of the title compound and the corresponding monophosphine oxide. This material was put in a dry 50 mL Schlenck flask under $N_2$, and diluted with o-oxylene (10 mL), and trichlorosilane (2 mL, 20 mmol) was added After heating with stirring at 70° C. for 2 hrs, the mixture was evaporated to dryness. The residue was taken up in dichloromethane and filtered on silica gel, to give another 2.0 g of the title compound (combined yield 5.2 g, 71% yield), identical to that obtained in Method (a).

The product of Example 5 is described below as (R)-HexaPhemp

EXAMPLE 6

(R)-3,3',4,4',5,5'-Hexamethyl-6,6'-bis(3,5-dimethylphenyl)phosphonylbiphenyl

The title compound was prepared by a reaction sequence analogous to Examples 1–5, $^{31}P$ NMR ($CDCl_3$), 162 MHz)·−13.0.

EXAMPLE 7

Synthesis of HexaPhemp-RuCl$_2$-Diamine Complexes

Representative procedure for (R)-HexaPhemp-RuCl$_2$-(S,S)-DPEN:

To a dry 25 ml Schlenck flask under nitrogen atmosphere and with stirring bar were added (R)-HexaPhemp (18 mg, 0.03 mol), [Ru(benzene)Cl$_2$]$_2$ (7.5 mg, 0.015 mmol) and dry, degassed dimethylformamide (1 mL). The flask was placed in an oil bath at 100° C. and the mixture stirred for 20 min (blood-red solution). After cooling down to room temperature (ca. 45 min), (S,S)-diphenylethylenediamine (DPEN) (7 mg, 0.033 mmol) was added and the mixture stirred at room temperature for 2 h. Dimethylformamide was evaporated off under reduced pressure and the resulting orange-yellow oil triturated with diethyl ether (2×1 mL) and evaporated off. The resulting crude powder was used as such for hydrogenation reactions. $^{31}P$—NMR ($CDCl_3$, 162 MHz)·45 2

The complexes (R)-HexaPhemp-RuCl$_2$-(R,R)-DPEN,(S)-HexaPhemp-RuCl$_2$-(S,S)-DPEN, (S)-HexaPhemp-RuCl$_2$-(R,R)-DPEN,(R)-HexaPhemp-RuCl$_2$-(R)-DAIPEN,(S), HexaPhemp-RuCl$_2$-(S,S)-DACH and (S)-HexaPhemp-RuCl$_2$-(R,R)-DACH were each prepared by a similar procedure DAIPEN is 1,1-dianisyl-2-isopropyl-1,2-ethylenediamine; DACH is trans-1,2-diaminocyclohexane

EXAMPLE 8

Enatioselective Hydrogenation of Acetophenone using Crude (R)-HexaPhemp-RuCl$_2$-Diamine Complexes In a 50 mL autoclave was placed a liner with stirring bar and (R)-HexaPhemp-RuCl$_2$-(R)-DIAPEN (2.2 mg, 0.002 mmol). The autoclave was closed purged 3 times with vacuum/nitrogen and five times with vacuum/hydrogen. A solution of acetophenone (720 mg, 6.0 mmol) in dry, degassed 2-propanol (3.0 mL) was added and the autoclave purged eight times with hydrogen. A solution of potassium t-butoxide in 2-propanol (1.0M, 0.1 mL) was added, the reactor purge again eight times with hydrogen and the pressure fixed at 120 psi (8 bar). The mixture was stirred vigorously at room temperature. After 20 min, hydrogen uptake was 44 psi (3 bar) and did not change in the next 10 min, indicating full conversion. The pressure was released, an aliquot taken and analysed. >99% conversion was achieved and (S)-1-phenylethanol obtained with 90% ee. GC: Chirasil DEX CB, 100° C. for 7 min, then 30° C./min to 200° C.:9.3 min (R), 9.5 min (S).

Similar experiments with (R)-HexaPhemp-RuCl$_2$-(S,S)-DPEN and (R)-HexaPhemp-RuCl$_2$-(R,R)-DPEN gave >99% conversion in 30 min. and 1 h and 48 and 86% ee respectively.

The ligand precursors, ligands and catalysts described in Examples 4 to 8 are assigned the absolute configuration R through correlation with published data on structurally related compounds.

EXAMPLE 9

Enantioselective Hydrogenation of Acetophenone Comparative Experiments

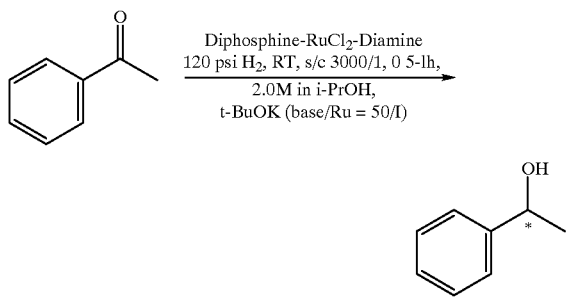

Using a standard reaction protocol according to Example 8 and the conditions depicted schematically, direct comparison was made between complexes of (R)-HexaPhemp, BINAP (1) and BIPHEP (2). From the results summarised in the following table, it is evident that the (R)-HexaPhemp complexes are superior with respect to both catalytic activity, as reflected by reaction times to effect complete substrate conversion, and enantioselectivity

| Catalyst | Time (hrs) | Conv. | Ee |
|---|---|---|---|
| [(R)-BINAP-Ru—Cl$_2$-(R,R)-DPEN | 9–14 | 100 | 83–84 |
| [(S)-BINAP-Ru—Cl$_2$-(S,S)-DACH | 3 | 85 | 82 |
| [(R)-BINAP-Ru—Cl$_2$-(R,R)-DAIPEN | 1 | 100 | 86 |
| [(R)-BIPHEP-Ru—Cl$_2$-(R,R)-DPEN | 12 | 100 | 84 |
| [(R)-HexaPhemp-Ru—Cl$_2$-(R,R)-DPEN | 1 | 100 | 86 |
| [(R)-HexaPhemp-Ru—Cl$_2$-(R,R)-DACH | 0.3 | 100 | 86 |
| [(R)-HexaPhemp-Ru—Cl$_2$-(R,R)-DAIPEN | 0 5 | 100 | 90 |

EXAMPLE 10

Asymmetric Hydrogenation of 2-methylquinoxaline using HexaPhemp-RuCl$_2$-diamine Complexes

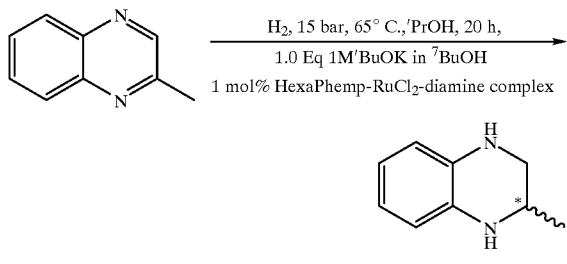

In a multi-well hydrogenation apparatus was placed a 20 mL liner with stirring bar and (S)-HexaPhemp-RuCl$_2$-(S,S)-DACH (5.8 mg, 0.006 mmol) The hydrogenation apparatus was purged with nitrogen and then pressurised to 20 bar with hydrogen. The pressure was released and this process repeated three times. To the cell containing the pre-catalyst was added, through the injection port, a solution of 2-methylquinoxaline (ex. Aldrich, 72 mg, 0.50 mmol) in 2-propanol (2 mL) The hydrogenation apparatus was purged (pressurized to 20 bar and then released) four times with hydrogen. To the cell containing the pre-catalyst and substrate was added 1 M potassium tert-butoxide in tert-butanol (0.5 mL, 0.50 mmol). The hydrogenation apparatus was purged (pressurized to 20 bar and then released) four times with hydrogen and pressurised to 15 bar with hydrogen. The mixture was stirred vigorously at 65° C. for 20 h. The pressure was released, the apparatus purged with nitrogen and an aliquot was analysed (trifluoroacetate derivatives). This show 94% substrate conversion and to give product of 81% ee GC. Chirasil DEX CB, 130° C. for 10 min, then 15° C./min to 200° C. Enantiomers·16.5 and 17.1 min.

EXAMPLE 11

[(S)-HexaPhemp-RuCl$_2$]$_2$NEt$_3$ Complex

[RuCl$_2$(COD)]$_n$ (44 mg, 0.157 mmol) and (S)-HexaPhemp (100 mg, 0.165 mmol) were placed in a 50 ml Youngs flask fitted with a double ended filter and a 25 ml Schlenk flask The entire apparatus was evacuated and back filled with N$_2$ three times to establish an inert atmosphere. Toluene (anhydrous, deoxygenated, 3.5 ml) and NEt$_3$ (0.35 ml) were then added and the system sealed. The reaction mixture was stirred at 140° C. for 4 h. Upon cooling to room temperature, no precipitate was observed. Hence, the reaction mixture was concentrated to approx. 2 ml and Et$_2$O (anhydrous, deoxygenated, 10 ml) added All volatiles were removed in vacuo to yield an orange powder. $^{31}$P and $^1$H NMR spectroscopy (sample prepared under nitrogen using dried and degassed CDCl$_3$) showed this to be a mixture of ruthenium-containing complexes with one major species consistent with previously reported complexes of the type [RuCl$_2$(Bisaryl-diphosphine)]$_2$NEt$_3$.

EXAMPLE 12

[(S)-HexaPhemp-Ru(CF$_3$CO$_2$)$_2$]Complex

[RuCOD(CF$_3$CO$_2$)$_2$]$_2$(0.033 mmol) and (S)-HexaPhemp (0.066 mmol) were placed in a 50 ml Schlenk flask. The entire apparatus was evacuated and back filled with N$_2$ three times to establish an inert atmosphere THF (anhydrous, deoxygenated, 10 ml) was added and the reaction mixture stirred at 40° C. for 5 h. The reaction was then reduced to dryness in vacuo and the resulting tan-coloured solid washed with hexane (10 ml). After drying in vacuo for 3 h, $^{31}$P{$^1$H} NMR spectroscopy (sample prepared under nitrogen using CDCl$_3$) showed the tan-coloured powder to be the desired complex; $^{31}$P NMR (CDCl$_3$, 162 MHZ): δ 55.6 (d), 49.5 (d).

EXAMPLE 13

Asymmetric Hydrogenation of a Cyclic Enamide

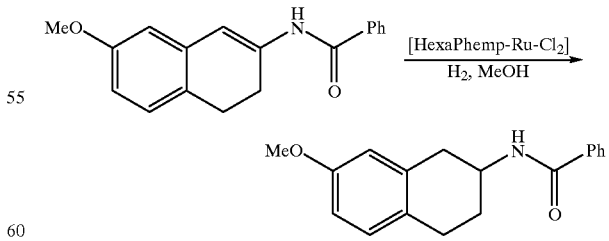

To a dry Schlenk flask under nitrogen atmosphere and with stirring bar were added (S)-HexaPhemp (32 mg, 0.053 mmol), [Ru(benzene)Cl$_2$]$_2$ (12.4 mg, 0.24 mmol) and dry, degassed dimethylformamide (1 ml). The mixture was stirred at 110° C. for 30 min and then concentrated under reduced pressure. Methanol (2×1 ml) was added to the residue and the resulting mixture was concentrated under reduced pressure after each addition. The residue was stored under nitrogen and used directly as a catalyst as follows.

A liner was charged with cyclic enamide (1 mmol; prepared according to the procedure described by Devocelle et al. Tetrahedron Lett. 1999, 40, 4551) and placed in a hydrogenation vessel. The vessel was flushed carefully with nitrogen several times, then 5 ml of degassed methanol was added. After stirring for a few minutes, the catalyst (0.01 mol %) was added as a solution in 1 ml of methanol. After stirring for a few minutes, the vessel was flushed 3 times with hydrogen (150 psi; 12 bar), and then the autoclave was pressured at 150 psi (12 bar) The reaction mixture was stirred at 60° C. for 20 h, and then allowed to cool at room temperature. Chiral HPLC analysis indicated 100% conversion of substrate to form amide produce of 86% ee

EXAMPLE 14

[(S)-HexaPhemp-Rh(COD)]BF$_4$

Under N$_2$, a CH$_2$Cl$_2$ solution (5 ml) of (S)-HexaPhemp (0.165 mmol) was added dropwise over 10 min to a stirred CH$_2$Cl$_2$ solution (5 ml) of [Rh(COD)$_2$]$_{BF4}$ (0.165 mmol) The reaction was left stirring under N$_2$ for 18 h during which time the reaction changed colour to a pale orange. The reaction was then reduced to dryness in vacuo and the resulting orange solid washed three times with Et$_2$O (4 ml) After drying in vacuo for 3 h, $^1$H, $^{13}$C and $^{31}$P{$^1$H} NMR spectroscopy (sample prepared under nitrogen using dried and degassed CDCl$_3$) showed the orange powder to be the desired complex; $^{31}$P NMR (CDCl$_3$, 162 MHZ)·δ 26.1 (s).

We claim:

1. An enantiomerically enriched compound of formula 5:

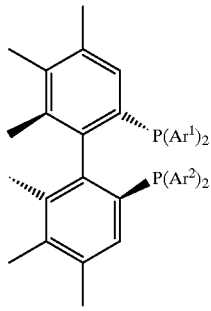

or the opposite enantiomer thereof, wherein Ar$^1$ and Ar$^2$ represent the same or different aromatic groups of up to 20 carbon atoms.

2. The compound, according to claim 1, wherein Ar$^1$=Ar$^2$.

3. The compound, according to claim 2, wherein Ar$^1$ and Ar$^2$ are each phenyl, optionally substituted with one or more alkyl or alkoxy groups.

4. The compound, according to claim 3, wherein Ar$^1$ and Ar$^2$ are each phenyl.

5. The compound, according to claim 3, wherein Ar$^1$ and Ar$^2$ are each 3,5-dimethylphenyl.

6. A transition metal complex of an enantiomerically enriched compound of formula 5:

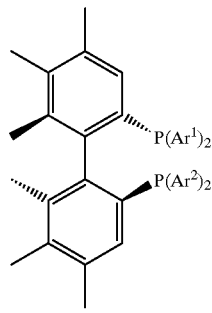

or the opposite enantiomer thereof, wherein Ar$^1$ and Ar2 represent the same or different aromatic groups of up to 20 carbon atoms.

7. The complex, according to claim 6, wherein the metal is ruthenium.

8. The complex, according to claim 7, having the formula Ru(5)X$_2$, wherein X is selected from the group consisting of halide, carboxylate and allylic radicals.

9. The complex, according to claim 7, having the formula Ru(5)X$_2$(DIA), wherein DIA is a chiral diamine and X is either halide or carboxylate.

10. The complex, according to claim 6, wherein the metal is rhodium.

11. A method for the stereoselective hydrogenation of a substrate, which is conducted in the presence of, as catalyst, a transition metal complex of an enantiomerically enriched compound of formula 5:

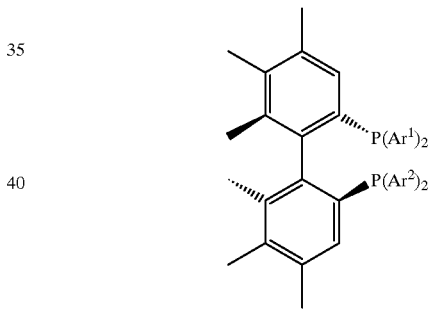

or the opposite enantiomer thereof, wherein Ar$^1$ and Ar$^2$ represent the same or different aromatic groups of up to 20 carbon atoms.

12. The method, according to claim 11, wherein the substrate has at least one C=O or C=N bond that is hydrogenated.

13. The method, according to claim 12, wherein the substrate is an imine and the product is a chiral amine.

14. The method, according to claim 12, wherein the substrate is a ketone and the product is a chiral alcohol.

15. The method, according to claim 11, wherein the substrate has at least one C=C bond that is hydrogenated.

16. The method, according to claim 11, wherein the substrate is prochiral and the product is generated in enantiomerically enriched form.

* * * * *